Feb. 2, 1960 J. P. TREMMEL ET AL Plant Pat. 1,901
PEACH TREE
Filed Nov. 6, 1958
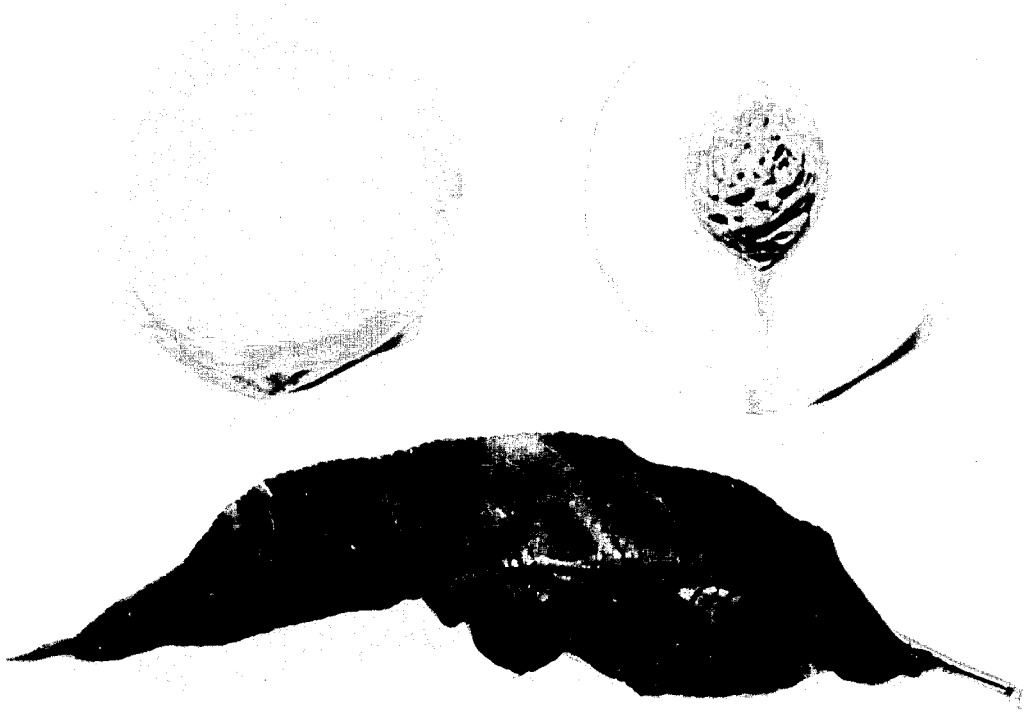
INVENTORS
John P. Tremmel & Minnie K. Tremmel
By Orville M. Kile
Plant Patent Agent.

United States Patent Office

Plant Pat. 1,901
Patented Feb. 2, 1960

1,901

PEACH TREE

John P. Tremmel and Minnie K. Tremmel,
Sigourney, Iowa

Application November 6, 1958, Serial No. 805,291

1 Claim. (Cl. 47—62)

Our present discovery is a new and improved variety of peach tree, producing yellow, freestone fruit of the type used largely for canning and freezing purposes. It is an open pollinated seedling of the peach tree variety which is the subject of plant patent application Serial Number 760, 821, filed September 12, 1958, but the male parent is not known. The seedling was found among some peach trees of the above variety on our farm near Sigourney, Iowa. Its vigor and the spreading nature of the tree caused us to watch it carefully for several years. The fourth year it bloomed and fruited, and we found it to have other desirable features which make a combination found in no other known peach variety. Outstanding among its qualities are its resistance to extreme cold, heavy production, and a fruit with thin skin, little fuzz, fine-grained flesh, and mild flavor.

This new variety has been asexually reproduced at our farm by means of budding, and the distinguishing characteristics appear to be permanent.

The accompanying illustration is a color photograph of a whole peach, a half peach with seed, and a leaf of this new variety, all in approximately natural size and color in the original. However, size of both fruit and leaf will vary depending on the amount of thinning done, the position on the tree and the growing conditions.

In the following detailed description, color plate designations refer to Ridgway's Color Standards and Nomenclature, while other colors mentioned refer to the usual dictionary meaning of the term.

*The tree*

Growth: Medium in size; very vigorous; spreading, having an underspread and many lateral branches.

Bearing habits: Begins bearing at an early age. Produces very large crops of fruit, even when subjected to low temperatures. Requires thinning in order to get a heavy crop of large-sized fruit.

Hardiness: Extremely hardy to low winter temperatures. Has set fruit following below-zero winter weather (even as low as minus 24 degrees Fahrenheit), when most other trees in the area were killed.

Leaves:

*Size.*—Medium-large, varying, but averaging about six inches long by 1½ inches wide.

*Type.*—Has globose glands.

*Color.*—Dark green, approximately Elm Green (Pl. XVII).

*Petiole.*—Short to medium.

*Shape.*—Somewhat lanceolate, with long, slender point and rounded base.

*Appearance.*—Smooth and shiny.

Blossoms:

*Size.*—Large, many with 2-inch spread.

*Color.*—Usually deep pink.

*Type.*—Self-pollinating.

*Cold resistance.*—Hardy to low winter temperatures. After winter temperatures of 22 degrees below zero F., and following a hard freeze with blossoms about 60 percent open, this variety had a set of fruit heavy enough to require considerable thinning.

*Season.*—Mid-April to early May in this vicinity.

*The fruit*

Form: Globular, with deep basin.

Size: Averages 2½ to 3 inches in diameter if properly thinned on the tree.

Ripening habit: Colors well ten days before hard-ripe stage. Clings well when ripe.

Keeping and shipping qualities: Excellent if picked in hard-ripe condition.

Skin:

*Character.*—Thin.

*Color.*—Basic color is between Primuline Yellow (Pl. XV) and Yellow Ochre (Pl. XV), with half to two-thirds of this covered with red from Peach Red to Carmine (both Pl. I).

*Adherence.*—Skin separates from flesh easily when fruit is ripe.

*Pubescence.*—Practically no fuzz is present.

Flesh:

*Texture.*—Fine-grained; firm but tender; very juicy.

*Flavor.*—Excellent; mild.

*Color.*—Yellow, approximately Apricot Yellow (Pl. IV), with very slight amount of red around pit. Does not brown in process of canning.

Stone:

*Type.*—Free under normal conditions of ripening.

*Size.*—Small to medium.

*Form.*—Plump.

*Surface.*—Deeply pitted.

*Color.*—Approximately Nopal Red to Garnet Brown (Pl. I).

*Comparison*

The variety known to us which is most like our new variety is the applicants' own variety of peach tree disclosed in their co-pending application Serial No. 760,821, filed September 12, 1958. The principal differences between the two varieties are as follows:

(1) The new variety of peach tree has larger flowers than the above said peach tree.

(2) Color of the flowers is darker.

(3) Color of the skin of the peach is not quite as dark red.

(4) Peach has a thinner skin.

(5) Peach has less fuzz.

(6) Flesh is finer grained.

(7) Flesh is milder in flavor.

(8) The new variety of peach tree has more lateral branches making it more spreading.

Having thus disclosed our discovery, we claim:

The new and distinct variety of freestone peach tree, substantially as herein shown and described, characterized particularly by its vigorous spreading growth; its early and prolific production of blossoms and fruit; its resistance to extreme cold; its large, dark pink blossoms; and its relatively large fruit with fine-grained, mild-flavored, yellow flesh and thin skin which colors early and is almost devoid of fuzz.

No references cited.